(12) United States Patent
Flanner et al.

(10) Patent No.: US 6,384,020 B1
(45) Date of Patent: May 7, 2002

(54) RAPID IMMEDIATE RELEASE ORAL DOSAGE FORM

(75) Inventors: Henry H. Flanner, Montgomery Village; Rong-Kun Chang, Rockville; Jill E. Pinkett, Baltimore; Sandra E. Wassink, Frederick; Lisa R. White, Damascus, all of MD (US)

(73) Assignee: Shire Laboratories, Inc., Rockville, MD (US)

( * ) Notice: Subject to any disclaimer, the term of this patent is extended or adjusted under 35 U.S.C. 154(b) by 0 days.

(21) Appl. No.: 09/611,098

(22) Filed: Jul. 6, 2000

Related U.S. Application Data

(60) Provisional application No. 60/143,903, filed on Jul. 14, 1999.

(51) Int. Cl.$^7$ .................................................. A61K 9/20
(52) U.S. Cl. .......................... 514/53; 654/690; 654/961; 424/465
(58) Field of Search .......................... 514/53, 654, 960, 514/961; 424/465

(56) References Cited

U.S. PATENT DOCUMENTS 5,501,861 A * 3/1996 Makino et al. .............. 424/464
5,846,568 A * 12/1998 Olinger et al. .............. 424/499
6,217,904 B1 * 4/2001 Midha et al. ................ 424/468

* cited by examiner

Primary Examiner—Frederick Krass
(74) Attorney, Agent, or Firm—Elliot M. Olstein; Raymond J. Lillie

(57) ABSTRACT

A pharmaceutical composition comprising lactitol and one or more amphetamine salts in a rapid release formulation.

12 Claims, No Drawings

RAPID IMMEDIATE RELEASE ORAL DOSAGE FORM

This Appln claims the benefit of U.S. Prov. App. No. 60/143,903, filed Jul. 14, 1999.

This invention relates to oral dosage forms with physicochemical stability and rapid drug release and the process to prepare them.

BACKGROUND OF THE INVENTION

Factors controlling the processing of drug formulations include 1) processability, i.e., adequate flow properties and satisfactory compression characteristics; 2) product attributes, i.e., appearance, tablet hardness, friability, color uniformity, content uniformity, and dissolution; and 3) stability, i.e., performance of the formulation over time. In order to realize an adequate stability profile for a particular dosage, the product must first overcome the first two hurdles.

Rapid immediate release pharmaceutical compositions typically contain carriers comprised of reducing-sugar based excipients, for example, lactose, dextrose, maltose, and fructose. The discoloration of dosage forms often occurs when these excipients are used with a drug having an amino functional group (Castello R A and Mattocks A M, *J Pharm Sci* 51(2): 106–108 (1962)). The Maillard reaction ("browning" reaction) is the reaction of amino groups of amino acids, peptides, proteins or other chemicals with the glycosidic hydroxyl group of sugars which results in the formation of brown pigments. This leads to degradation and discoloration of formulations and leads to failure to meet the stability requirement of the dosage form.

As alternatives to the reducing sugar based excipients, less water soluble excipients, such as dicalcium phosphate and microcrystalline cellulose, have been used to avoid the Maillard reaction. However, for certain dosage forms, such as tablets, these excipients are not able to provide the desired processing properties (such as compressibility) and product attributes (such as rapid release).

In particular, it would be desirable to possess a pharmaceutical composition which avoids the occurrence of the Maillard reaction for compositions containing active agents with amino functional groups which composition will have chemical and physical stability. It further would be desirable to maintain the rapid release properties of a pharmaceutical formulation in a compressed tablet formulation.

It is an object of the present invention to provide a rapid release pharmaceutical composition having chemical and physical stability in a tablet formulation.

SUMMARY OF THE INVENTION

The present invention relates to a pharmaceutical composition comprising (1) at least one amphetamine as a pharmaceutically active agent, and (2) lactitol. The applicants have found that the use of lactitol, a polyol, in formulations containing active agents having functional amine moieties provides a pharmaceutical formulation with the processability, product attribute and stability characteristics required for the administration of the dosage form. The use of polyols with amine containing active compounds will not trigger the Maillard reaction. The polyol is present in the formulation in an amount effective to provide the desired solubility and hydration properties required for an immediate release formulation.

In a preferred embodiment, the formulation is a compressed tablet. It has been discovered that the use of lactitol in the pharmaceutical composition of the present invention advantageously facilitates the compression of the composition into a tablet. The direct compression method is a preferred method because it is less costly, less time-consuming, and has improved stability. However, wet granulation is also suitable.

Lactitol (4-O-(-D-Galactopyranosyl-D-glucitol monohydrate) is a non-hygroscopic, disaccharide sugar alcohol derived from lactose which heretofore has been used in food products, for example, as a sweetener. Lactitol provides chemical and physical stability to dosage forms with amine containing actives.

Incorporation of lactitol into the pharmaceutical composition advantageously facilitates the compression of the composition into a tablet and facilitates fast dissolution of the tablet matrix, due to its high water solubility.

In a preferred embodiment, lactitol is used as a carrier for a tablet formulation wherein the active comprises a mixture of amphetamine salts, i.e., d-amphetamine sulfate, d,l-amphetamine aspartate, d-amphetamine saccharate, d,l-amphetamine sulfate. In a particularly preferred embodiment, the mixture of amphetamine salts is present in a 1:1:1:1 ratio.

Accordingly, an embodiment of the present invention provides a rapid release pharmaceutical composition comprising a mixture of amphetamine salts and lactitol in tablet form. In a preferred embodiment lactitol is used in combination with at least one or more other direct compression excipients. In a particularly preferred embodiment lactitol is used in combination with microcrystalline cellulose.

DETAILED DESCRIPTION OF THE INVENTION

Pharmaceutical actives which may be employed in the practice of the invention are those containing an amine functional group, which for example include, but are not limited to, amphetamines, phenylpropanolamine and its salts, carbidopa and levodopa.

In one embodiment of the invention the pharmaceutical actives are amphetamines including amphetamine base, all chemical and chiral derivatives and salts thereof. In a preferred embodiment of this invention a mixture of amphetamine salts is employed, i.e., d-amphetamine sulfate, d,l-amphetamine aspartate, d-amphetamine saccharate, d,l-amphetamine sulfate. In a particularly preferred embodiment, the mixture of amphetamine salts is present in a 1:1:1:1 ratio.

The pharmaceutical composition of the invention may further comprise bulking agents, disintegrating agents, antiadherants, glidants, lubricants, colorants and binding agents.

The bulking agents employed herein can be microcrystalline cellulose, for example, AVICEL® (FMC Corp.) or EMCOCEL® (Mendell Inc.); dicalcium phosphate, for example, EMCOMPRESS® (Mendell Inc.); calcium sulfate, for example, COMPACTROL® (Mendell Inc.); and starches, for example, STARCH 1500.

As disintegrating agents there may be employed herein microcrystalline cellulose, starches, crospovidone, for example, POLYPLASDONE XL® (International Specialty Products); sodium starch glycolate, for example, EXPLOTAB® (Mendell Inc.); and croscarmellose sodium, for example, AC-DI-SOL® (FMC Corp.).

Antiadherants and glidants employed herein can include talc, corn starch, silicon dioxide, sodium lauryl sulfate, and metallic stearates.

Lubricants employed herein can be magnesium stearate, calcium stearate, sodium stearate, stearic acid, sodium stearyl fumarate, sterotex, talc, colloidal silica dioxide, waxes and the like.

Binding agents employed herein can include but are not limited to polyvinyl pyrollidone, starch, methyl cellulose, hydroxypropyl methylcellulose, carboxymethyl cellulose, and the like.

The present invention is preferably in tablet form. The pharmaceutical composition of the present invention can also be produced as tablets in the form of hard gelatin capsules or packaged into sachets. Tablets prepared using lactitol may be used as chewable tablets, due to lactitol's clean taste, sweetness, and non-cariogenic property.

The present invention is preferably formulated into a tablet prepared using methods known in the art including a wet granulation method and a direct compression method. In a preferred embodiment the tablets are prepared using the direct compression method.

The direct compression method offers a number of potential advantages over a wet granulation method, particularly with respect to the relative ease of manufacture. Factors limiting the use of a direct compression method are 1) processability, i.e., adequate flow properties and satisfactory compression characteristics; and 2) product attributes, i.e., appearance, tablet hardness, friability, color uniformity, content uniformity, and dissolution. In order to realize an adequate stability profile via a direct compression method, the product must first overcome these two hurdles.

In dissolution testing, 100% dissolution of amphetamine salts from tablets containing lactitol can be easily achieved in less than 15 minutes. This is advantageous over previously known methods of preparing formulations of compressed tablets which utilize water-insoluble excipients alone as a tablet matrix material. These tablet do not dissolve rapidly in water because the low porosity of the compressed tablets hinders water penetration into the matrix.

Accordingly, in one aspect of the invention, lactitol is used in combination with one or more other direct compression excipients. In a preferred embodiment lactitol is used in combination with microcrystalline cellulose, for example, AVICEL® (FMC Corp.). In a preferred embodiment lactitol and microcrystalline cellulose are present in an amount of from about 2 to about 5 (lactitol) and from about 0.25 to about 1.75 for microcrystalline cellulose. The most preferred range is Lactitol from 3 to 4, and microcrystalline cellulose from 0.5 to 1.5. These numbers represent the amount in the pharmaceutical product composition of weight ratios or percent.

It has been found that other binary or ternary mixtures of direct compression excipients including starches, various grades of microcrystalline cellulose and polyols other than lactitol, such as mannitol and sorbitol, did not provide the required formulation processing characteristics for amphetamine tablets. For example, in general, soft tablets (tablet hardness less than target 4 kp) were produced even at high compression forces. For example, the mixture of Starch 1500: Mannitol 2080LF exhibited poor flow properties and sticking problems, which hinder the compression process. The mixture of Starch 1500: Lactitol also showed irregular flow properties. The ternary mixture of Starch 1500: Lactitol: Avicel PH 302 showed comparable successful performance characteristics to those of the Avicel/lactitol formulation.

Other problems such as tablet capping, color non-uniformity, and punch sticking, were observed. Surprisingly, after trying numerous mixtures of direct compression excipients, the formula containing the mixture of Avicel: Lactitol was identified as a meeting the required processability and product performance characteristics for amphetamine tablets.

EXAMPLES

The compositions of Example 1–4 are prepared using a direct compression method. The blending and tabletting process for the manufacture of the tablets of the present invention and comprise the following steps:

a) Sieve the tablet ingredients, i.e. drug substance, color, and lactitol, through a 20-mesh stainless steel screen;
b) Change a suitable blender with screened materials;
c) Blend for 10 minutes;
d) Sieve the remaining ingredients (except for magnesium stearate) through a 20-mesh stainless steel screen and add to already blended ingredients;
e) Blend for 20 minutes;
f) Sieve the lubricant through a 40-mesh stainless steel screen and adding to the blend;
g) Blend for 5 minutes;
h) Compress the blend into tablets on a rotary press using appropriate tooling; and
i) Optionally apply a coating onto the compressed tablets.

Example 1

The table below lists the ingredients and amount for the formulation of amphetamine immediate-release blend used to produce amphetamine immediate-release tablets, 5 mg.

| Ingredients | Composition (%) | mg/Tablet | Amount (g) |
| --- | --- | --- | --- |
| d-Amphetamine Sulfate | 1.25 | 1.3 | 937 |
| d,l-Amphetamine Aspartate | 1.25 | 1.3 | 937 |
| d-Amphetamine Saccharate | 1.25 | 1.3 | 937 |
| d,l-Amphetamine Sulfate | 1.25 | 1.3 | 937 |
| Lactitol | 40.00 | 41.6 | 30,000 |
| Lactitol | 33.65 | 35.1 | 25,315 |
| Microcrystalline Cellulose | 20.00 | 20.8 | 15,000 |
| Colloidal Silicon Dioxide | 0.29 | 0.3 | 216 |
| Magnesium Stearate | 0.96 | 1.0 | 721 |
| Total | 100 | 104.0 | 75,000 |

Example 2

The table below lists the ingredients and amount for the formulation of amphetamine immediate-release blend used to produce amphetamine immediate-release tablets, 10 mg.

| Ingredients | Composition (%) | mg/Tablet | Amount (g) |
| --- | --- | --- | --- |
| d-Amphetamine Sulfate | 1.23 | 1.3 | 919 |
| d,l-Amphetamine Aspartate | 1.23 | 1.3 | 919 |
| d-Amphetamine Saccharate | 1.23 | 1.3 | 919 |
| d,l-Amphetamine Sulfate | 1.23 | 1.3 | 919 |
| FD&C Aluminum Lake Blue#1 | 0.39 | 0.8 | 288 |
| Lactitol | 40.00 | 83.2 | 30,000 |
| Lactitol | 33.45 | 69.6 | 25,099 |
| Microcrystalline Cellulose | 20.00 | 41.6 | 15,000 |
| Colloidal Silicon Dioxide | 0.24 | 0.5 | 180 |
| Magnesium Stearate | 1.01 | 2.1 | 757 |
| Total | 100 | 208.0 | 75,000 |

Example 3

The table below lists the ingredients and amount for the formulation of amphetamine immediate-release blend used to produce amphetamine immediate-release tablets, 20 mg.

| Ingredients | Composition (%) | mg/Tablet | Amount (g) |
| --- | --- | --- | --- |
| d-Amphetamine Sulfate | 2.45 | 5.1 | 1,839 |
| d,l-Amphetamine Aspartate | 2.45 | 5.1 | 1,839 |
| d-Amphetamine Saccharate | 2.45 | 5.1 | 1,839 |
| d,l-Amphetamine Sulfate | 2.45 | 5.1 | 1,839 |
| FD&C Aluminum Lake Blue#1 | 0.39 | 0.8 | 288 |
| Lactitol | 40.00 | 59.4 | 30,000 |
| Lactitol | 28.56 | 83.2 | 21,419 |
| Microcrystalline Cellulose | 20.00 | 41.6 | 15,000 |
| Colloidal Silicon Dioxide | 0.24 | 0.5 | 180 |
| Magnesium Stearate | 1.01 | 2.1 | 757 |
| Total | 100 | 208.0 | 75,000 |

Example 4

The table below lists the ingredients and amount for the formulation of amphetamine immediate-release blend. The blend is then compressed on a rotary tablet press to produce amphetamine immediate-release tablets, 30 mg.

| Ingredients | Composition (%) | mg/Tablet | Amount (g) |
| --- | --- | --- | --- |
| d-Amphetamine Sulfate | 2.45 | 7.65 | 1,839 |
| d,l-Amphetamine Aspartate | 2.45 | 7.65 | 1,839 |
| d-Amphetamine Saccharate | 2.45 | 7.65 | 1,839 |
| d,l-Amphetamine Sulfate | 2.45 | 7.65 | 1,839 |
| Lactitol | 40.00 | 124.8 | 30,000 |
| Lactitol | 28.94 | 90.3 | 21,707 |
| Microcrystalline Cellulose | 20.00 | 62.4 | 15,000 |
| Colloidal Silicon Dioxide | 0.26 | 0.8 | 192 |
| Magnesium Stearate | 0.99 | 3.1 | 745 |
| Total | 100 | 312.0 | 75,000 |

Example 5

The table below lists the ingredients and amount for the formulation of amphetamine immediate-release blend. The blend is then filled into hard gelatin capsules using an automatic capsule-filling machine to produce amphetamine immediate-release capsules, 20 mg.

| Ingredients | Composition (%) | mg/Tablet | Amount (g) |
| --- | --- | --- | --- |
| d-Amphetamine Sulfate | 2.45 | 5.1 | 1,838 |
| d,l-Amphetamine Aspartate | 2.45 | 5.1 | 1,838 |
| d-Amphetamine Saccharate | 2.45 | 5.1 | 1,838 |
| d,l-Amphetamine Sulfate | 2.45 | 5.1 | 1,838 |
| Lactitol | 40.00 | 83.2 | 30,000 |
| Lactitol | 23.95 | 48.8 | 17,960 |
| Microcrystalline Cellulose | 20.00 | 41.6 | 15,000 |
| Croscarmellose Sodium | 5.00 | 10.4 | 3,750 |
| Colloidal Silicon Dioxide | 0.24 | 0.5 | 180 |
| Magnesium Stearate | 1.01 | 2.1 | 758 |
| Total | 100 | 208.0 | 75,000 |

Example 6

The formulation of this embodiment is prepared using a wet granulation method. The active agent, lactitol, and other excipients are granulated with a granulating fluid, e.g., isopropyl alcohol, ethyl alcohol, and water, in a planetary mixer, high shear mixer or fluidized bed granulator. Binding agents are in granulating fluid or in dry mix. The wet granules a re dried in an oven or fluidized-bed dryer, subsequently sieved through a suitable screen to obtain free-flowing granules. The resulting granules are blended with a suitable lubricant and glidant and lubricated granules are compressed into tablets on a rotary press using appropriate tooling. If desired, a coating is applied onto compressed tablets.

The table below lists the ingredients and amount for the formulation of amphetamine immediate-release granulates. The blend is compressed on a rotary tablet press to produce amphetamine immediate-release tablets, 30 mg.

| Ingredients | Composition (%) | mg/Tablet | Amount (g) |
| --- | --- | --- | --- |
| d-Amphetamine Sulfate | 2.45 | 7.65 | 1,839 |
| d,l-Amphetamine Aspartate | 2.45 | 7.65 | 1,839 |
| d-Amphetamine Saccharate | 2.45 | 7.65 | 1,839 |
| d,l-Amphetamine Sulfate | 2.45 | 7.65 | 1,839 |
| Lactitol | 50.00 | 156.0 | 37,500 |
| Croscarmellose Sodium | 5.00 | 15.6 | 3,765 |
| Microcrystalline Cellulose | 30.70 | 95.78 | 23,025 |
| Polyvinyl pyrollidone | 3.00 | 9.36 | 2,250 |
| Colloidal Silicon Dioxide | 0.50 | 1.56 | 375 |
| Magnesium Stearate | 1.00 | 3.12 | 750 |
| Total | 100.00 | 312.0 | 75,000 |

What is claimed is:

1. A pharmaceutical composition comprising a tablet, said tablet including (i) a pharmaceutical active selected from the group consisting of amphetamine base, salts, chemical and chiral derivatives thereof, and mixtures thereof; (ii) lactitol; and (iii) micro crystalline cellulose.

2. The composition of claim 1 wherein said pharmaceutical active comprises a mixture of amphetamine salts.

3. The composition of claim 2 wherein said amphetamine salts are selected from the group consisting of d-amphetamine sulfate, d,l-amphetamine aspartate, d-amphetamine saccharate, and d,l-amphetamine sulfate.

4. The composition of claim 3 wherein said d-amphetamine sulfate, d,l-amphetamine aspartate, d-amphetamine saccharate, and d,l-amphetamine sulfate are present in said composition in a ratio of 1:1:1:1.

5. The composition of claim 1 wherein said lactitol and said microcrystalline cellulose are present in said composition at a ratio of lactitol to microcrystalline cellulose of 2–5:0.25–1.75.

6. The composition of claim 5 wherein said lactitol and said microcrystalline cellulose are present in said composition at a ratio of lactitol to microcrystalline cellulose of 3–4: 0.5–1.5.

7. The composition of claim 1 and further comprising an antiadherant or glidant.

8. The composition of claim 7 wherein said antiadherant or glidant is selected from the group consisting of talc, corn starch, silicon dioxide, sodium lauryl sulfate, and metallic stearates.

9. The composition of claim 1 and further comprising a lubricant.

10. The composition of claim 9 wherein said lubricant is selected from the group consisting of magnesium stearate, calcium stearate, sodium stearate, stearic acid, sodium stearyl fumarate, sterotex, talc, colloidal silicon dioxide, and waxes.

11. The composition of claim 1 and further comprising a binding agent.

12. The composition of claim 11 wherein said binding agent is selected from the group consisting of polyvinyl pyrrolidone, starch, methyl cellulose, hydroxypropyl methylcellulose, and carboxymethyl cellulose.

\* \* \* \* \*